US007258850B2

(12) United States Patent
Rubsamen et al.

(10) Patent No.: US 7,258,850 B2
(45) Date of Patent: *Aug. 21, 2007

(54) METHODS AND COMPOSITIONS FOR TREATING ERECTILE DYSFUNCTION

(75) Inventors: Reid M. Rubsamen, Alamo, CA (US); Robert Cole, Alamo, CA (US); James Blanchard, El Granada, CA (US); Jeffrey Schuster, Berkeley, CA (US); Lawrence Linn, Walnut Creek, CA (US); John Thipphawong, Belmont, CA (US)

(73) Assignee: Aradigm Corporation, Hayward, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 10/685,746

(22) Filed: Oct. 14, 2003

(65) Prior Publication Data

US 2004/0208829 A1 Oct. 21, 2004

Related U.S. Application Data

(63) Continuation-in-part of application No. 09/813,100, filed on Mar. 19, 2001, now Pat. No. 6,632,419, which is a continuation-in-part of application No. 09/563,773, filed on May 2, 2000, now Pat. No. 6,428,769.

(60) Provisional application No. 60/132,472, filed on May 4, 1999.

(51) Int. Cl.
*A61K 9/12* (2006.01)
*A61K 9/14* (2006.01)
*A61K 31/56* (2006.01)

(52) U.S. Cl. .......................... 424/45; 424/46; 424/43; 424/489; 424/434; 514/573; 514/253; 514/638

(58) Field of Classification Search ................ 424/45, 424/46, 489, 434, 43; 514/573, 284, 253, 514/638; 128/200.14
See application file for complete search history.

(56) References Cited

U.S. PATENT DOCUMENTS

| 4,895,719 | A | * | 1/1990 | Radhakrishnan et al. ...... 424/45 |
| 5,426,107 | A | | 6/1995 | Bell et al. |
| 5,536,714 | A | | 7/1996 | Kojima et al. |
| 5,756,071 | A | | 5/1998 | Mattern et al. |
| 5,877,216 | A | * | 3/1999 | Place et al. .................. 514/573 |
| 6,342,251 | B1 | * | 1/2002 | Illum et al. .................. 424/501 |
| 6,395,744 | B1 | * | 5/2002 | Adams et al. ................ 514/284 |
| 6,579,968 | B1 | * | 6/2003 | Blood et al. .................. 530/312 |
| 6,632,419 | B2 | * | 10/2003 | Rubsamen et al. ............ 424/43 |
| 6,803,031 | B2 | * | 10/2004 | Rabinowitz et al. .......... 424/45 |
| 2002/0107182 | A1 | | 8/2002 | Blood et al. |
| 2003/0119714 | A1 | | 6/2003 | Naylor et al. |
| 2004/0081624 | A1 | * | 4/2004 | Nguyen et al. ................ 424/44 |
| 2004/0204440 | A1 | * | 10/2004 | Staniforth et al. ........... 514/295 |

FOREIGN PATENT DOCUMENTS

| EP | 1 097 711 | 5/2001 |
| JP | 06 211675 | 8/1994 |
| WO | WO9428902 | * 12/1994 |
| WO | WO97/29735 | 8/1997 |
| WO | WO98/29096 | 7/1998 |
| WO | WO98/31346 | 7/1998 |
| WO | WO98/34595 | 8/1998 |
| WO | WO 00/40226 | 7/2000 |

OTHER PUBLICATIONS

S.R.Davis, "The therapeutic use of androgens in women", Journal od steroid biochemistry and molecular biology 69 (1999), 177-184.*
Drug Information Handbook, Lacy et al, LEXi-COMP, Inc. Edition 1993, pp. 867-869.*
Drug Facts and Comparison, Drug Information on sildenafil citrate, 1998 (obtained on-line).*
S. R. Davis, "The therapeutic use of androgens in women", Journal of steroid biochemistry and molecular biology 69 (1999) 177-184.*
DIALOG® databse—File 351:Derwent WPI: "Non-occlusive, percutaneous, or transdermal drug delivery system—having active agent, safe and approved sunscreen as penetration enhancer, and optional volatile liquid.".
Ko et al., "Emulsion formulations of testosterone for nasal administration" J. Microencapsulation, 15(2):197-205 (1998).
Edwards et al., "Large Porous Particles for Pulmonary Drug Delivery" Science, 276:1868-1871 (Jun. 20, 1997).
Kaplan et al., "Safety and Efficacy of Sildenafil In Postmenopausal Women With Sexual Dysfunction" Urology, 53 (3):481-486 (1999).
Fava et al., "An Open Trial of Oral Sildenafil in Antidepressant-Induced Sexual Dysfunction" Psychother. Psychosom. 67:328-331 (1998).

* cited by examiner

*Primary Examiner*—Johann Richter
*Assistant Examiner*—Mina Haghighatian
(74) *Attorney, Agent, or Firm*—Karl Bozicevic; Bozicevic, Field & Francis LLP

(57) ABSTRACT

Methods are provided for increasing libido and/or treating erectile dysfunction in a man. The methods include the administration of a formulation testosterone alone, another fast-acting drug to treat erectile dysfunction or a combination of the testosterone and the other drug where at least one is delivered by aersolization. The formulation is preferably aerosolized and inhaled into a patient's lungs where particles of testosterone and/or the fast-acting erectile dysfunction drug deposits on lung tissue and then enter the patient's circulatory system.

17 Claims, No Drawings

METHODS AND COMPOSITIONS FOR TREATING ERECTILE DYSFUNCTION

CROSS-REFERENCES

This application is a continuation-in-part of U.S. patent application Ser. No. 09/813,100 filed on Mar. 19, 2001, to be issued as U.S. Pat. No. 6,632,419 which is a continuation-in-part of U.S. patent application Ser. No. 09/563,773 filed on May 2, 2000, now issued U.S. Pat. No. 6,428,769 and claims the benefit of U.S. Provisional Patent Application Ser. No. 60/132,472 filed on May 4, 1999, all of which are incorporated herein by reference in their entirety.

FIELD OF THE INVENTION

This invention relates generally to methods of treating sexual dysfunction in humans. Such methods include treating women with a decreased libido, treating men with reduced libido and/or having a decreased level of serum testosterone, and treating men having erectile dysfunction. More specifically, the invention relates to acute, bolus non-invasive administration of testosterone to enhance libido and/or a drug formulation to treat erectile dysfunction over a discrete period of time.

BACKGROUND OF THE INVENTION

The presence of a normal amount of libido, defined as the urge to engage in sexual activity, is an important component of an individual's well-being. In both men and women the primary naturally occurring hormone responsible for libido is testosterone. In males, the baseline testosterone level is a relatively constant throughout life, decreasing slowly in old age. Abnormally low levels of testosterone also Occur in male hypogonadism and are similarly associated with lack of libido and inability to produce or sustain erections. In contrast, women elaborate testosterone only as part of the process of ovulation. Each maturing follicle produces testosterone at the mid-point of the menstrual cycle, consistent with observations that female libido peaks with ovulation. As a woman ages, the number of maturing follicles per month decreases, and there is a decreasing total amount of testosterone produced. A common complaint of post-menopausal women is decreased libido. This decrease in libido is characterized by a lack of interest in sexual intercourse, the lack of ability to achieve orgasm, or decrease in intensity of orgasm. It is important to note that this decrease in libido is often associated with a profound sense of loss of a once normal and active interest in sexual activity. Low levels of testosterone in, e.g., hypogonadal men are associated with lack of libido and absence of erections. They respond to therapy with exogenous testosterone (Cunningham et al., *J Clin Endocrinol Metab*, (March 1990) 70:792-7; Behre et al., *J Clin Endocrinol Metab*, (November 1992) 75:1204-10; and women also respond to testosterone therapy, see Tuiten et al., *Arch. Gen. Phychiatry*, (February 2000) 57:149-153.

Clinicians frequently confronted with the problem of managing female patients presenting with decreased libido have limited tools to address the problem. Testosterone is available as an oral preparation and can be given, for instance, in combination with estrogen to restore testosterone levels. However, the replacement of the once pulsatile endogenous delivery of testosterone with the sustained blood level of the hormone produces unwanted side effects. Women taking testosterone for a few weeks typically begin to complain of the emergence of secondary sexual characteristics such as unwanted body hair, oily hair, and, with prolonged a use, deepening voice. For this reason, oral testosterone replacement therapy is not a practical solution for most patients with decreased libido.

Other forms of testosterone replacement therapy for women are being explored. A transdermal patch capable of delivering a steady rate of testosterone is being tested for use in women. As with oral testosterone replacement therapy, the study state blood levels of testosterone produced via transdermal delivery are likely to be associated with the same side effect profile issues.

It is recognized that testosterone in males and females decreases with age (Expert Opin. Pharmacother 2003 February; 4(2):183-90; Human Biology, May 1980, Vol. 52, No. 2, pages 181-01,91), and that sexual motivation in men with low testosterone as well as mood and well-being in post-menopausal women is associated with the levels of exogenously introduced testosterone (Psychosomatic Medicine volume 47, No. 4, 1985). Further, providing intravenous testosterone to men and women as part of clinical studies is known (Am Heart J 2002 February; 143(2):249-56; American Journal of Obstetrics and Gynecology, December 1986 pages 1288 to 1292).

Various formulations of testosterone are currently commercially available to treat sexual dysfunction in men. A transdermal patch for men is sold by Alza Corporation under the name of Testoderm®. An injectable for intramuscular injectable is sold by Bristol-Meyers-Squibb Company under the name Delatestryl®, and by Star under the name Virilon® IM. While these dosage forms may increase steady state levels of testosterone in men, they do not result in the physiologically correct pulsatile release that occurs in men with normal testosterone production. A bolus delivery of testosterone provides an approximation to the pulsatile delivery yielding short brief peaks that can provide the physiological stimulus for increase of sexual desire and improved erectile function.

Current therapies and those under development for erectile dysfunction (ED) include phosphodiesterase (PDE) inhibitors (e.g., Viagra (sildenafil), Cialis), dopamine receptor agonists (e.g., apomorphine), melanocortin receptor agonists, intracavernous therapies (e.g., alprostadil, papaverine, phentolamine, vasoactive intestinal peptide), growth hormone-releasing peptide receptor agonists, 5-hydroxytryptamine (5-HT; serotonin) receptor agonists, alpha-adrenoceptor antagonists, topical therapies (e.g., alprostadil), guanylyl cyclase activators, rho-kinase antagonists and inhibitors of neuropeptide Y.

In cases where a single therapy for ED is ineffective, combination therapy may be effective, especially when two or more mechanisms the drugs affect different sites of action are simultaneously employed. For example, the combination of a drug that acts centrally, e.g., on the central nervous system (CNS), with a drug that acts peripherally has been proposed (Andersson and Hedlund, Int. J. Impot. Res. 14(Suppl.1): S82-S92, 2002). For example in a rat model, the erectile response to apomorphine, which acts via the CNS, has been prolonged by sildenafil, which acts peripherally (Andersson et al. J. Urol. 161: 1707-12, 1999). The use of a combination therapy involving inhaled testosterone, which acts on the CNS, with any other class of treatment, whether it acts centrally or peripherally, having therapeutic potential may be more effective than either treatment alone.

SUMMARY OF THE INVENTION

The present invention provides for various methods of treating sexual dysfunction in humans, including reduced libido in women, reduced libido in men, and erectile dysfunction in men.

In one embodiment, a method is provided for increasing the libido of a woman over a discrete period of time (e.g., 30-240 minutes) by the administration of testosterone. This method does not maintain therapeutic levels of testosterone over long periods, e.g., days, weeks or months. Because the method of the invention only maintains therapeutic levels over a short period, the adverse side effects of long-term testosterone treatment are avoided.

In another embodiment, a method is provided for increasing libido and/or treating erectile dysfunction in a man by the administration of testosterone or another drug formulation including, but not limited to, sildenafil, including sildenafil citrate and other salts of sildenafil as well as other drug formulations and combinations of testosterone; sildenafil, and/or other drugs.

The testosterone formulation used with the present invention may be comprised of a reduced version of testosterone having been reduced by 5α-reductase to 5γ-dihydroxytestosterone which is delivered in a bolus dose. The testosterone formulation may be administered in a variety of different ways, e.g., may be aerosolized preferably producing particles which have a size in a range of from about 1 to 3 microns which can be inhaled into areas of the lung where they can readily enter the blood stream.

With the methods of the present inventions, an aerosol containing a drug is inhaled into the lungs of a patient. Once inhaled, particles of the drug deposit on lung tissue and from there enter the patient's circulatory system and thereby increase the patient's serum testosterone level. In certain-embodiments, the aerosol comprises testosterone or its reduced version 5-γ-dihydrotestorone. The percentage increase in the patient's testosterone level will vary depending on the needs of the patient. However, the patient's normal baseline serum testosterone level is preferably increased 25% or more and more preferably 100% or more. By preferably providing the testosterone in a reduced form, i.e., 5α-dihydroxytestosterone because the delivery is by inhalation the patient's serum level of an active form of the hormone is quickly raised to a desired level, e.g., in thirty minutes or less, more preferably fifteen minutes or less. When the patient's blood serum level of the active form of the hormone is raised to a desired level the patient's libido is increased. The increased level gradually subsides (as the hormone is metabolized and cleared) thereby avoiding the adverse side effects generated by maintaining enhanced hormone levels over long periods. Where the aerosol comprises a drug for treating erectile dysfunction, the effect of the drug is realized in less time than when delivered by other routes of administration such as oral, and preferably is realized in less than 30 minutes, more preferably in less then 20 minutes, still more preferably in less than 10 minutes.

An aspect of the invention is a method of increasing the libido of an adult human female patient by the administration of a bolus dose of testosterone which quickly increases the level of testosterone in the patient for a relatively brief time.

Another aspect of the invention is a method of treatment whereby testosterone or derivative thereof is aerosolized, inhaled and provided to the circulatory system of the patient at levels sufficient to increase libido (over a short period of time) and propensity for orgasm.

Another aspect of the invention is to combine bolus delivery of testosterone with additional treatment such as a topical cream applied to the vaginal area to increase blood flow to that area.

An advantage of the invention is that the testosterone levels are raised within minutes of administration (preferably 30 minutes or less) and return to normal levels within hours—preferably in less than four hours.

Another advantage is that the administered testosterone is quickly metabolized allowing the patient's testosterone levels to return to normal thereby avoiding the adverse effects of long-term administration.

Another advantage of the invention is that erectile dysfunction and sexual dysfunction are treated more rapidly, as compared to other delivery routes, e.g., orally or transdermally, due to the rapid absorption of small molecules through the lung when inhaled, in order that the user need not plan ahead before engaging in sexual activity Another advantage of the invention that the total dose of erectile dysfunction and sexual dysfunction compounds delivered can be reduced because of the rapid absorption from the lung, which will lead to efficacious plasma levels for shorter periods of time, as compared to other administration by other means, e.g., oral and transdermal delivery. This will allow for reduction in side effects, and cost of therapy Another advantage is that the time to onset of action will be independent of the amount and time of prandial intake.

A feature of the invention is that aerosolized particles of testosterone having a diameter of about 0.5 to 8 microns (preferably 1-3 microns) are created and inhaled deeply into the lungs thereby enhancing the speed and efficiency of administration.

It is an object of this invention to describe the utility of delivering testosterone or dihydrotestosterone by inhalation as a means of treating women with decreased libido and/or decreased propensity to have orgasms.

It is another object of this invention to describe liquid formulations (which includes suspensions) of testosterone and derivatives thereof such as 5α-dihydrotestosterone appropriate for pulmonary delivery.

It is another object of this invention to describe how testosterone or dihydrotestosterone delivered via the lung can quickly increase plasma levels substantially beyond baseline levels for the patient.

It is another object of this invention to describe the blood levels of testosterone or dihydrotestosterone required for rapid onset of a normal to enhanced libido in men or women with baseline decreased libido.

It is another object of this invention to describe the time course of inhalation of testosterone or dihydrotestosterone and the onset of increased libido in women or men suffering from decreased libido.

It is another object of this invention to describe how the pulsatile delivery of testosterone or specifically dihydrotestosterone-as replacement therapy for women with decreased libido is associated with a decreased incidence of side effects (secondary sexual characteristics) commonly associated with traditional testosterone replacement therapy which produces a steady state level of the hormone.

It is another object of this invention to provide men with a pulsatile delivery of testosterone which approximates the natural physiological release of testosterone, in contrast to the existing delivery systems for testosterone such as transdermal patches or long acting injections containing esters of testosterone.

Other aspects of the invention include bolus (i.e., fast delivery and short acting effects) delivery of testosterone by any means including nasal delivery, rapid transdermal delivery which may be with absorption enhancers, and/or abrasive transdermal systems, microneedle systems, and topical creams, which systems may be used in various combinations.

The delivery of testosterone by inhalation provides, for the first time, the means for non-invasively delivering clinically relevant amounts of testosterone on demand near the time of planned intercourse.

It is an object of the invention to provide a method of treatment of erectile dysfunction in a patient comprising the steps of aerosolizing a formulation comprising sildenafil-citrate or other salts of sildenafil, e.g., acetate, or other composition, inhaling the aerosolized formulation into the lungs of a patient, and allowing the particles of sildenafil citrate to deposit on lung tissue and enter the patient's circulatory system.

It is an object of the invention to provide an aerosolized formulation comprised of sildenafil citrate or another salt of sildenafil, e.g., acetate, or other composition, and a carrier, the aerosol comprising particles having a diameter in the range of about 1.0 micron to 5.0 microns, making up 50% or more of the aerosol particles.

It is an object of the invention to provide a kit comprising an aerosol delivery device and a formulation comprising a testosterone or testosterone derivative (DHT), sildenafil citrate or other salts of sildenafil, or other compositions suitable for the treatment of sexual dysfunction or erectile dysfunction, or a combination thereof.

It is an object of the invention to provide a kit comprising an aerosol delivery device and a formulation comprising a testosterone or testosterone derivative (DHT) to be used either alone or in combination with any therapy already in use or currently under development to treat ED including: phosphodiesterase (PDE) inhibitors (e.g., Viagra, Cialis), dopamine receptor agonists (e.g., apomorphine), melanocortin receptor agonists, intracavernous therapies (e.g., alprostadil, papaverine, phentolamine intracavernous therapies (e.g., alprostadil, papaverine, phentolamine, vasoactive intestinal peptide), growth hormone-releasing peptide receptor agonists, 5-hydroxytryptamine (5-HT; serotonin) receptor agonists, alpha-adrenoceptor antagonists, topical therapies (e.g., alprostadil), guanylyl cyclase activators, rho-kinase antagonists, oxytocin, oxytocin receptor agonists, and inhibitors of neuropeptide Y.

It is an object of the invention to provide a kit comprising two aerosol delivery devices and two formulations, a first formulation comprising a testosterone for use by women, and a second formulation comprising a testosterone, sildenafil-citrate or other salt of sildenafil, e.g., acetate, or other composition, or a combination thereof, for use by a man.

These and other aspects, objects, advantages, and features of the invention will become apparent to those skilled in the art upon reading this disclosure.

DEFINITIONS

The terms "testosterone", "a testosterone" and the like are used interchangeably here and are intended to mean the naturally occurring hormone known as testosterone having the chemical name 17-β-hydroxyandrost-4-en-3-one which may be isolated and purified from nature or synthetically produced in any manner. The terms also comprise pharmaceutically acceptable esters, i.e., compounds where the "H" of the "OH" group is replaced with an alkyl group, e.g., propionate, cypionate and enanthate. Other pharmaceutically acceptable derivatives include methyltestosterone, methandrostenolone, fluovymesterone and danazol. A number of pharmaceutically useful derivatives of testosterone which are intended to be encompassed by the term testosterone as used here are disclosed within the Physician's Desk Reference (most recent edition) as well as Harrison's Principles of Internal Medicine. In addition, applicants-refer to U.S. Pat. Nos. 5,536,714 issued Jul. 16, 1996; 5,824,668 issued Oct. 20, 1998; 3,980,638 issued Sep. 14, 1996; 4,031,117 issued Jun. 21, 1977; 4,085,202 issued Apr. 18, 1978; 4,197,286 issued Apr. 8, 1980; 4,507,290 issued Mar. 26, 1985 and 5,622,944 issued Apr. 22, 1997 all of which are incorporated herein by reference to disclose and describe testosterone derivatives and formulations.

The terms "reduced testosterone," "dihydrotestosterone" and the like are used interchangeably here and are intended to encompass the commonly occurring reduced version of testosterone having been reduced by 5α-reductase to 5α-dihydroxytestosterone which is also referred to here as dihydrotestosterone (DHT) or simply "a testosterone." A dihydrotestosterone may be isolated from nature but is preferably synthetically produced and purified. Testosterone USP is a white or creamy-white crystalline powder having a molecular weight of 288.43.

The terms "androgen," "androgenic hormone" and the like are used interchangeably here and are intended to encompass any agent which stimulates activity of the accessory male sex organs and specifically is intended here to cover "a testosterone" as well as a "reduced testosterone" as defined above.

The terms "diameter", "particle diameter" and the like are used interchangeably herein to refer to particle size as given in the "aerodynamic" size of the particle. The aerodynamic diameter is a measurement of a particle of unit density that has the same terminal sedimentation velocity in air under normal atmospheric conditions as the particle in question. This is pointed out in that it is difficult to accurately measure the diameter of small particles using current technology and the shape of such small particles may be continually changing. Thus, the diameter of one particle of material of a given density will be said to have the same diameter as another particle of the same material if the two particles have the same terminal sedimentation velocity in air under the same conditions. In connection with the present invention it is important to have particles which do not have too large of a diameter so that the particles can be inhaled deeply into the lungs and thereby deposited on lung tissue and transferred into the patient's circulatory system. It is equally important not to have particles which are too small in that such particles would be inhaled into the lungs and then exhaled without depositing on the lung tissue in the same manner that particles of smoke can be inhaled and exhaled with only a small amount of the particles being deposited on the lung tissue. An acceptable range for particle diameter is in the range of 0.5 to 12 microns, preferably 0.5 to 8 microns and more preferably 1 to 3 microns.

DETAILED DESCRIPTION OF THE PREFERRED EMBODIMENTS

Before the devices, formulations, and methodology of the present invention are described, it is to be understood-that this invention is not limited to the particular device, components, formulations and methodology described, as such may, of course, vary. It is also to be understood that the terminology used herein is with the purpose of describing particular embodiments only, and is not intended to limit the scope of the present invention which will be limited only by the appended claims.

It must be noted that as used herein and in the appended claims, the singular forms "a", "an", and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

All publications mentioned herein are incorporated herein by reference to described and disclose specific information for which the reference was cited in connection with. The publications discussed herein are provided solely for their stated disclosure prior to the filing date of the present application. Nothing herein is to be construed as an admission that the invention is not entitled to antedate such publications by virtue of prior invention. Further, the actual publication date may be different from that stated on the publication and as such may require independent verification of the actual publication dates.

Some embodiments of the invention involve the bolus delivery of testosterone or dihydrotestosterone. Thus, the invention is generally and specifically described by referring to testosterone and/or dihyrotestosterone specifically. However, the invention is more generally applicable to any androgen.

INVENTION IN GENERAL

Despite the fact that steady state delivery of testosterone as replacement therapy for women experiencing decreased libido is inherently prone to producing unwanted side effects, the use of pulsatile testosterone replacement therapy to mimic the normal elaboration of this hormone during ovulation has not been explored. The use of testosterone replacement therapy for brief courses of treatment has been attempted, however the slow rate of absorption of methyl testosterone from pills has limited its utility. In order to replace the missing testosterone in a therapeutically effective manner, it is necessary to provide a rapid pulse of bioavailable testosterone to the patient on demand. In this way, testosterone could be replaced by the patient as needed coincident with the desire to engage in sexual activity. Similarly, the current methods of delivery of testosterone to men do not provide physiologically correct pharmacokinetics. Similarly, the current methods of delivery of testosterone and other compositions for the treatment of ED do not approximate endogenous, physiologically correct pharmacokinetics.

It is not surprising that clinical studies evaluating the effect of acute, on demand testosterone replacement therapy in women with decreased libido have not been attempted. The only tool currently available for a true pulsatile, rapid onset replacement therapy is intravenous administration. Although preparations of testosterone appropriate for intravenous administrations have been available for some time, intravenous cannulation as the means for gaining access to the circulation for the administration of testosterone on demand is inconsistent with the desire for women to be able to modulate their libido in concert with the course of their daily lives.

Precision delivery of small molecule drugs via the lung for systemic effect is possible. An electronic inhaler capable of delivering a liquid formulated drug stored in a unit dose packages has been described. Devices and container formulations of solutions and suspensions to be aerosolized are described in U.S. Pat. Nos. 5,544,646; 5,718,222; 6,123,068; 6,014,969; 5,660,166, and 5,823,178 as well as the publications cited in these patents. Other types of aerosol delivery devices which contain pressurized propellants can also be used, e.g., see U.S. Pat. Nos. 5,404,871; 5,542,410; and 5,826,570 as well as the publications cited in these patents. Nebulizers and dry powder inhaler devices can also be used. A formulation of testosterone or dihydrotestosterone can be prepared for a bolus delivery including an aerosol delivery.

The quantitative delivery of testosterone or dihydrotestosterone, on demand by a woman prior to initiation of sexual intercourse, provides a mechanism for testosterone replacement therapy which is unlikely to be associated with side effects precipitated by chronic delivery of the drug. The present invention differs from most methods of treatment in that the method taught here preferably obtains an effective increase in testosterone quickly and thereafter has the drug metabolized so that there is no longer an effect on the patient. Thus, while most drugs are delivered to obtain a relatively constant therapeutic effect the method of the present invention obtains a very short-term effect. In providing a useful method of increasing libido the patient's testosterone level is preferably raised in 30 minutes or less or more preferably five minutes or less and is metabolized out of the patient's system to below therapeutic levels in four hours or less or preferably two hours or less.

Administration can be by a variety of different routes including intravenous, intranasal, buccal, transdermal and intrapulmonary. However, intravenous injection can be an uncomfortable route of administration. Transdermal delivery is generally too slow but with permeation enhancers and/or a large surface area one can obtain the desired "bolus" administration. Creating an aerosol and delivery by inhalation is the preferred route of administration for convenience and quickly raising blood levels. Any two or more of these different routes of administration may be combined to enhance the desired effect. Further, one route of administration (e.g., transdermal) may be used to increase basal levels over long term (below levels causing adverse side effects) while using another route (e.g., inhalation) to increase levels more quickly over a much shorter term to obtain the desired short term increase in libido.

While particularly applicable to post menopausal woman, the use of testosterone replacement therapy to modulate libido could be of value to women still of child bearing age. Disappearance of or reduction of the libido has been described in women who are continuing to ovulate. The reduction in libido may be due to therapy including the use of birth control pills which contain hormones. Therefore, acute administration of testosterone to significantly raise blood levels for discrete periods has potentially widespread application in women across a wide range of ages.

The baseline serum testosterone level of a normal adult human female is generally below about 1 ng/ml with modest changes through the menstrual cycle (Geobelmann et al., *Am J. Obstet. Gynecol.* 119:445 (1974)) with general fluctuation between about 0.3 to 0.5 ng/ml. However, adult human females with polycystic ovarian disease have ovarian vein testosterone levels of 20 to 65 ng/ml and peripheral venous levels of about 7.5 ng/ml (Dupon et al., *Am. J. Obstet. Gynecol.* 115:478 (1973)). Abnormally high levels of testosterone over long periods are associated with acne and hirsutism.

To maintain normal testosterone levels an adult human female will produce about 0.25 mg of testosterone per day as compared to about 5-6 mg/day produced by a normal adult male to maintain a normal adult male testosterone level of 3 to 10 ng/ml. Because women produce such small amounts of testosterone the administration of very small amounts will dramatically increase the patient's normal levels. In accordance with the present invention 0.05 mg to 5 mg, preferably 0.25 to 2 mg and more preferably about 1 mg of testosterone is administered to the circulatory system of the patient. Administration of such amounts to the circulatory system may require aerosolizing larger amounts due to inefficiencies in the aerosol delivery system.

Testosterone can be administered orally. However, after oral administration it is absorbed from the gut into the portal blood and degraded promptly by the liver. Also, the absorption is relatively slow. Thus, insignificant amounts reach the patient's systemic circulation. Testosterone can also be administered parenterally but, because of its poor aqueous solubility, alcoholic solutions generally are necessary. These alcohol-based formulations may cause unpleasant sensations at the site of injection. Further, when so administered it is rapidly absorbed and metabolized making it difficult to sustain effective levels in plasma over time. In view of such, effective therapy has been carried out using means of delivery where testosterone is slowly absorbed (e.g., dermal patches) or when the testosterone is chemically modified to retard absorption and/or catabolism.

The present invention preferably uses intrapulmonary delivery to avoid first pass liver metabolism and to obtain quick infusion into the patient's systemic circulatory system. Further, the method of the present invention does not require maintaining increased testosterone levels over long periods. Accordingly, chemical modification to retard absorption and/or catabolism are not required or desired.

The present invention administers sufficient testosterone by inhalation to temporarily raise the patient's libido, increase the patient's propensity for orgasm, and thereafter allow the patient's testosterone level to return to a level normally experienced by the patient.

THERAPIES TO TREAT ERECTILE DYSFUNCTION

Testosterone therapy as described herein can be used in combination with other therapies intended to increase or enhance libido. Such therapies include but are not limited to herbal preparations and vitamin supplements.

There are known methods and formulations for treating female sexual dysfunction (FSD) as well as male erectile dysfunction (ED). These known methods and formulations can be used in combination with or independently of the bolus androgenic hormone delivery methodology disclosed and described here.

Formulations and methods of treating ED include those disclosed and described in U.S. Pat. Nos. 5,718,917; 6,156,753; 6,037,346; and 6,007,824 which include oral and local administration of sildenafil citrate. Other formulations and methods of treating ED are disclosed and described in U.S. Patent Application Publication No. 2003/0171393 which include the topical application of sildenafil salts where the salts are organic salts, including but not limited to oxalate, tartrate, maleate, succinate, citrate, glycinate, lysinate, or inorganic anions including but not limited to nitrate, chloride, sulphate, phosphate. Other pharmaceutically acceptable salts are disclosed in the Handbook of Pharmaceutical Salts: Properties Selection, and Use; P. Heinrich Stahl, and Camille G. Wermuth, Eds.; Wiley V C H, Weinheim, Federal Republic of Germany (2002); pp. 334-345.

Formulations and methods of treating FSD include those disclosed and described in U.S. Pat. Nos. 6,046,240; 5,877,216; 5,891,915; 5,698,589; 6,089,909; and 6,169,914 which include the administration of vasodilating drugs to the vaginal area to increase blood flow to that area.

INDICATIONS

The method of the invention has broad applicability to both the male and female populations. However, its use is specifically indicated in six categories.

First, post-menopausal women who have experienced all or any of (1) decreased levels of testosterone; (2) decreased libido; and (3) decreased propensity to experience orgasm.

Second, women of child bearing age who have experienced all or any of (1) decreased levels of testosterone; (2) decreased libido; and (3) decreased propensity to experience orgasm.

Third, women of child bearing age being treated with birth control pills who have experienced all or any of (1) increased levels of estrogen relative to testosterone resulting in either or both of (2) decreased libido and (3) decreased propensity to experience orgasm.

Fourth, men with reduced libido.

Fifth, men having a decreased level of serum testosterone.

Sixth, men having erectile dysfunction.

In the first three categories it is not desirable to administer sufficient amounts of a testosterone so as to raise the patient's testosterone level continually over long periods of time. For example, it is not desirable to administer testosterone several times per day for several days. Such will raise testosterone levels over long periods and result in adverse side effects including acne, and increased growth of body hair. Bolus delivery to men facilitates a more physiological means of delivery of testosterone than that afforded by the currently marketed transdermal patches.

DOSING

The amount of a testosterone administered will vary based on a factor such as the age, weight and baseline testosterone level of the patient. Initially, small doses, e.g. about 0.25 mg, is administered for women. If the desired result is obtained no further dosing is provided. If the desired effect is not obtained additional 0.25 mg doses can be administered up to 2.0 mg. If the patient finds that larger doses are needed then for further treatment the patient may be provided with doses of 0.5 mg, 1.0 mg or 2.0 mg. The amount aerosolized may be substantially greater than the amount administered if the interpulmonary delivery device is inefficient. Thus, the device and method efficiencies must be taken into consideration when titrating the doses.

When testosterone enters the circulatory system of a human patient it is readily reduced via 5α-reductase to 5α-dihydrotestosterone. Thus, when referring to increasing a patient's testosterone level this disclosure is referring to combined levels of testosterone and 5α-dihydroxytestosterone present in the patient's serum. The present invention includes the administration of 5α-dihydroxytestosterone which is the active molecule. The invention also includes the administration of testosterone derivatives provided such derivatives increase libido and do not result in unacceptable adverse effects.

Obtaining a result such as increased libido may be difficult to ascertain. Some placebo effect will be experienced by some patients and others may continuously administer doses in an attempt to obtain a more enhanced effect. To avoid undesirable side effects from overdosing or from dosing to frequently the delivery device may be controlled by a suitable lockout system such as taught in U.S. Pat. Nos. 5,507,277; 5,694,919; and 5,735,263. Such a system can prevent release of more than a given amount of drug at a single dosing event and/or restrict the number of dosing events within a given period of time. The restrictions-are designed to prevent the patient from experiencing adverse secondary effects.

FORMULATIONS/DEVICES

Pharmaceutical grade testosterone can be produced as a white or creamy white powder. The pure powder is aerosolized and inhaled by itself or with the use of a dry powder inhaler (DPI) device. However, it is desirable to formulate the crystals with an excipient to provide small particles of dry powder which do not stick together. Also, the doses of testosterone can be so small (<1 mg) which would make filling and metering of the doses difficult without blending testosterone with a "carrier" material such as lactose particles. The testosterone particles preferably have an aerodynamic diameter in a range of from about 1 to 10 microns more preferably 1 to 5 microns and still more preferably about 1 to about 3 microns. Testosterone could be also dissolved in a suitable solvent together with some excipients and then could be recovered as solid or porous particles by removal of the solvent e.g. by spray drying, or freeze-drying or using precipitation followed by removal of the solvent. Methods of formulating dry powders and dry powder inhaler devices are disclosed in U.S. Pat. Nos. 5,826,633; 5,814,607; 5,785,049; 5,780,014; 5,775,320; 5,740,794; and Des. 390,651 all of which are incorporated by reference to describe and disclose such.

Testosterone, sildenifil citrate, and some other drugs for treatment of ED and SD are relatively insoluble in water. Accordingly, to create a solution a solubilizer (e.g., one of several cyclodextrines or phospholipids) or an organic solvent such as ethanol is used. Alternatively, a microsuspension in water with or without ethanol can also be produced. The solution is aerosolized and inhaled. The solution can be placed in a low boiling point propellant in a pressurized canister and released using a conventional metered dose inhaler (MDI) device. Preferably, the MDI device is modified so that the aerosolized dose is released each time at the same inspiratory flow rate and inspiratory volume. When this is done the patient is more likely to receive the same dose each time. A device for obtaining repeatable dosing with an MDI canister is taught in U.S. Pat. No. 5,404,871 issued Apr. 11, 1995.

In accordance with the present invention it is preferable to load the solution into a container which opens to a porous membrane. When the formulation is moved through the membrane it is aerosolized. Such containers are taught in U.S. Pat. No. 5,497,763 issued Mar. 12, 1996. The container is loaded into a device and delivered via a method as taught in U.S. Pat. No. 5,823,178 issued Oct. 10, 1998 both of which patents are incorporated herein by reference to describe and disclose containers, devices and methods of drug delivery by inhalation.

Aerosol drug delivery devices vary but generally are comprised of (1) a container for the drug e.g. testosterone; (2) a means for aerosolizing the drug; and (3) a mouthpiece from which the aerosol is inhaled. The aerosol can be any small particles dispersed in air, e.g. a cloud of a dry powder or a fine spray of liquid formulation. Nebulizers, metered dose inhalers (MDIs) and dry powder inhalers (DPIs) are the most well known devices for creating an aerosol. Less conventional devices known as electrohydrodynamic aerosol devices as taught in U.S. Pat. No. 4,358,059; PCT WO 99/07478; and 98/03267 can also be used to create an aerosol in the method of the invention.

Nasal or buccal formulations could be used for nasal or buccal delivery, or transdermal patches, preferably with absorption enhancers to achieve "bolus" delivery of testosterone into the blood stream.

AEROSOL ADMINISTRATION OF SILDENAFIL AND OTHER COMPOSITIONS

Similarly, agents such as sildenafil citrate and other salts of sildenafil, e.g., sildenafil acetate (U.S. Pat. No. 5,426,107 and U.S. Pat. No. 5,250,534), or other compositions useful in the treatment of SD or ED can also be administered to women or men by the methods of the instant invention, alone or in combination with testosterone.

Sildenafil citrate, also termed VIAGRA™, is typically administered in tablet form to men experiencing erectile dysfunctions resulting from peripheral vascular disease. The tablet is taken orally about thirty (30) minutes to four (4) hours before sexual activity.

The typical oral dose of sildenafil is 25-100 mg per day. As described above, such doses can be administered to the lungs through the use of aerosolized aqueous solutions or as a dry powder. Because of the more rapid absorption from the lung, lower doses can be delivered to achieve the same effect, albeit for a shorter period of time.

The advantage of aerosolized delivery is a faster result as compared to oral administration. Further, the delivery of sildenafil citrate either orally or via an aerosol can be combined with the bolus delivery of a testosterone formulation.

The can be formulated alone or as an admixture with a testosterone for simultaneous bolus delivery.

In an embodiment, men in need of supplemental testosterone and experiencing erectile dysfunction can administer the drugs either simultaneously or sequentially. The dosage of testosterone will typically be sufficient to raise the serum testosterone level of the man to a normal range, that being about 200-1000 ng/dL.

The formulation can be administered to male or female patients and may be administered alone or in combination with an aerosolized dose of testosterone.

In one embodiment of the invention the sildenafil citrate is administered orally and the testosterone is administered by aerosol about 30-60 minutes after the oral administration of sildenafil citrate. The oral administration of sildenafil citrate is an administration in advance of a sexual event and after allowing time to achieve a therapeutic effect on increasing blood flow the patient is dosed with testosterone via aerosol. The testosterone enhances the libido and the sildenafil citrate enhances the patient's ability to perform and/or achieve orgasm. The aerosolized administration of testosterone could also be in used combination with other drugs administered by aerosolization or by other means, e.g., alprostadil administered topically, used in the treatment of various sexual dysfunctions, e.g., erectile dysfunction. Alternatively, such drugs may be delivered according to the methods of the present invention as a monotherapy (i.e., without testosterone).

Examples of such fast-acting drugs for treating erectile dysfunction which may be used according to the methods of the present invention include but are not limited to PDE5 inhibitors, melanocortin receptors, oxytocin and oxytocin receptor agonists, inhibitors of a neuropeptide Y (NPY); dopamine receptor agonists (e.g., apomorphine), melanocortin receptor agonists, intracavemous therapies, growth hormone-releasing peptide receptor agonists, 5-hydroxytryptamine receptor agonists, alpha-adrenoceptor antagonists, topical therapies, guanylyl cyclase activators, and rho-kinase antagonists.

PDE5-inhibitors are known to treat-erectile dysfunction as disclosed in U.S. Patent Application Publication No. 2003/0144296. PDE5 converts cyclic guanosine monophosphate (cGMP) and cyclic adenosine monophosphate (cAMP) to monophosphate. cGMP is a major intracellular effector of smooth muscle relaxation, facilitates increased blood flow, and elicits erection. By reducing the breakdown of cGMP, PDE5 prolongs action of cGMP. Vardenafil (Nuivi, Bayer/GSK) and Tadalfil (Cialis, Lilly ICOS LLC) are two PDE5 inhibitors that may be administered by the methods of the present invention. Vardenafil has been administered orally from 5 to 20 mg, with onset of the therapeutic effect occurring at about 40 minutes after administration and lasting for about 4 hours. Tadalafil has been administered orally from 10 to 20 mg, with onset of the therapeutic effect occurring at about 16 minutes after administration and lasting up to about 36 hours.

In animal models, the α-melanocyte stimulating hormone (α-MSHs) and the adrenocorticotropic hormone (ACTH) induce erection, ejaculation, grooming, stretching, and yawning (Argiolas et al, Brain Res. Bull. 51: 425-32, 2000). Most, if not all, activities of α-MSH/ACTH peptides are mediated through specific subtypes of the melanocortin (MC) receptors in the hypothalamic periventricular region (Argiolas et al, Brain Res. Bull. 51: 425-32, 2000; Vergoni et al, Eur. J. Pharmacol. 362: 95-101, 1998). It has recently been shown the MC4 receptor causes erection in rats. (Shadnick et al, Presentation at Society of Neuroscience, 2001). Melatonan II/PT-141 (Palatin Technologies, Inc.) is a synthetic cyclic heptapeptide analog of α-MSH and is a nonselective MC receptor agonist. It is known to be a potent inducer of erection in men with non-organic ED when injected subcutaneously; however, yawning and stretching, and in some cases severe nausea and vomiting limit is use (Wessells et al, Int. J. Impot. Res. 12 (Supp. 4): S74-S79, 2000). Intranasal administration of this formulation, however, does not appear to exhibit these side effects. With a dose of 4-20 mg administered intranasally, therapeutic onset takes place in about 34-63 minutes of dosing and lasts for as long as 138 minutes (Diamond et al., Int. J. Impot. Res. 12 (Supp. 4): S20-21, 2002).

Oxytocin and 5-hydroxytryptamine (5-HT; serotonin) receptor agonists are other compounds known to induce erection in rats by increasing nitric oxide (NO) synthase and smooth muscle relaxation (Argiolas et al, Eur. J. Pharmacol. 130: 265-272, 1986; Hayes et al, Int. J. Impot. Res. 12(Supp. 3): S62, 2000). However, there is currently no known development of oxytocin or analogues thereof for treating ED.

Growth hormone (GH)-releasing peptide receptors also act by way of the oxytocinegic pathway to increase NO synthase and muscle relaxation. A new class of peptides that release GH is more potent than endogenous GH-releasing hormone. Studies involving the injection of 20-200 ng into the paraventricular nucleus of the hypothalamus in rats have induced erection indistinguishable from those of dopamine receptor agonists, oxytocin, or N-methyl-D-aspartic acid (Melis et al, Int. J. Impot. Res. 12: 255-262, 2000).

Apomorphine, a dopamine D1 and D2 $D_1$ and $D_2$ receptor agonist, provides a short-acting therapeutic effect although it has a narrow therapeutic window (Lal et al, Prog. Neuropsychopharmacol. Biol. Psychiatry 13: 329-339, 1989). However, the duration of erectile response in rats has been prolonged in combination with sildenafil (Andersson et al, J. Urol. 161: 1707-12, 1999). A nasal form of apomorphine is being developed (Nastech) to treat male and female sexual dysfunction in humans.

α-adrenoceptor (AR) antagonists have the effect of blocking $\alpha_1$-AR and/or $\alpha_2$-AR on smooth muscle and thereby decreasing the sympathetic tone of penile erectile tissues, causing relaxation of the smooth muscle. Suitable AR antagonists include phentolamine mesylate (Vasomax® by Zonagen), thymoxamine (moxisylyte), yohimbine (α2 antagonist). It has been found that the nitrosylation of moxisylyte and yohimbine have produced more potent compounds (Sáenz de Tejada et al., J. Pharmacol. Exp. Ther. 290: 121-128, 1999). Additionally, NitroMed is developing oral medications that combine the NO donor L-arginine and the alpha-blocker yohimbin to treat the full range (mild to severe) of ED sufferers.

The most commonly used intracavemous drug therapies in the U.S. are prostagladin $E_1$ (alpostadil) alone and in combination with papaverine and phentolamine (Trimex). Prostagladin $E_1$ increases intracellular concentrations of cAMP in the corpus cavernosum, thereby enhancing vasodilation. While these drugs have been highly effective in treating ED, they have certain disadvantages including the requirement that they be administered by injection and they carrying the risk of causing priapism and scarring in the penis (Porst, J. Urol. 155:802-815, 1996; Fallon, Urol. Clin. North Am. 22: 833-845, 1995). Vasoactive intestinal peptid (VIP) is another intracavernous drug that is potent as a smooth muscle relaxant with an onset between 2 to 5 minutes after dosing and lasting up to 2.5 hours (data cited at www.Senetek.com).

Guanylyl cyclases (GC) receptors are another type of formulation for treating ED. GC exists in soluble (sGC) and particulate (GC-B) forms in all cell types, and helps to catalyze the conversion of GTP to cGMP. YC-1 (3-(5'-hydroxymethyl-2'furyl)-1-benzyl-indazole) directly activates sGC by increasing affinity for GTP leading to increased cGMP in smooth muscle, which is the major intracellular effector of smooth muscle relaxation. Studies have shown that YC-1 administered intracavernously elicited dose-dependent erection in rats (Andersson and Hedlund Int. J. Impot. Res. 14(Suppl.1): S82-S92, 2002). BAY-41-2272 (pyrazolpyridine), another GC receptor, has been shown to cause relaxation of human and rabbit corpus carvernosum more potently than YC-1 by stimulating sGC in an NO-independent manner without relying upon cGMP breakdown (Kalsi et al, Int. J. Impot. Res. 14(Suppl. 3): S2, 2002).

Rho-kinase antagonists, such as Y-27632 (Mitsubishi Pharma, Osaka, Japan), applied topically stimulated erection in rats possibly by increasing corpus caveronsum pressure. Specific inhibition of Rho-kinase in the cavernosal circulation leads to erection by a mechanism not dependent on NO-cGMP signaling (Nature Medicine, 7:119, 2001).

Depending on the type of drug, the dosage required, the time of therapeutic onset and the duration of such therapeutic onset will vary. The dosages required for aerosolized delivery are likely to be less than those indicated for oral delivery.

Other oral, injectable and topical drugs are and will become available for the treatment of sexual dysfunctions and such drugs (e.g., vasodilators)-can be used in combination with aerosolized delivery of testosterone to obtain enhanced results. It is noted that although such drugs may, by themselves, facilitate sexual activity they do not affect libido. Accordingly, a truly enhanced effect is obtainable by combining a drug, which increases blood flow to a desired area, with aerosolized delivery of testosterone, which increases libido.

KITS

In an embodiment of the invention, a kit is provided for use by a healthcare provider, and more preferably for use by a patient. An exemplary kit will provide a hand-held aerosol delivery device and at least one dose, preferably one to about one hundred, more preferably one to thirty doses of a testosterone for use by a women. In an embodiment, the kit will comprise a hand-held aerosol delivery device and at least one dose, preferably one to about one hundred, more preferably one to thirty doses of a testosterone for use by a man. In an embodiment, the kit will provide a hand-held aerosol delivery device and at least one dose, preferably one to about one hundred, more preferably one to thirty doses of an admixture of testosterone and sildenafil citrate for use by a man. In an embodiment, the kit will contain a hand-held aerosol delivery device and at least one dose, preferably one to about one hundred, more preferably about one to thirty doses of sildenafil citrate for use by a man.

In an embodiment, a kit is provided which comprises two hand-held delivery devices, wherein a first delivery device comprises at least one dose, preferably one to one hundred doses, of a testosterone for use by a woman. The second delivery device comprises at least one dose, preferably one to one hundred doses, of a testosterone, sildenafil citrate, or a combination thereof for use by a man. Such a kit is intended for use by a couple in need of such treatment.

The kit of the invention can be comprised of various combinations of drugs and drug delivery devices. However, the kit will preferably be comprised of an aerosol drug delivery device which comprises a container which holds one or a plurality of doses of testosterone, a means for aerosolizing the testosterone and a mouthpiece from which the aerosolized testosterone may be inhaled. This device is present in the kit with another drug. For example, the kit may comprise a container of sildenafil citrate or related drug which obtains a response similar to sildenafil citrate. The other drug may be administered orally or topically but is preferably in a container which can be loaded into the device used to deliver the testosterone by inhalation. Thus, a preferred kit will comprise a drug delivery device which can generate an aerosol for inhalation and a plurality of containers of testosterone which can be loaded into the device and a plurality of containers of a vasodilator such as sildenafil citrate which can be loaded into the device.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

What is claimed is:

1. A method of treating erectile dysfunction in a patient, comprising the steps of:

diagnosing a human male patient as having erectile dysfunction;

aerosolizing a formulation comprising sildenafil;

inhaling the aerosolized formulation into the lungs of the human male patient; and allowing particles comprising sildenafil to deposit on lung tissue, and enter the patient's circulatory system in an amount sufficient to treat the erectile dysfunction of the human male patient.

2. The method of claim 1, further comprising:

administering a bolus dose of an androgenic hormone to the patient.

3. The method of claim 2, wherein the administering of the androgenic hormone is by:

aerosolizing a formulation comprised of an androgenic hormone;

inhaling aerosolized androgenic hormone; and allowing the androgenic hormone to deposit on lung tissue.

4. The method of claim 3, wherein the androgenic hormone is selected from the group consisting of testosterone and dihydrotestosterone.

5. The method of claim 1, wherein the aerosolized particles are comprised of particles having a diameter in a range of from about 1 to about 5 microns.

6. The method of claim 1, wherein the formulation further comprises a testosterone. a melanocortin receptor agonist, an a-adrenoceptor antagonist, aiprostadil, papaverine, phentolamine, vasoactive intestinal peptide, guanylyl cyclases, a rho-kinase antagonist, oxytocin, an oxytcicin receptor agonist, an inhibitor of neuropeptide Y, and a combination thereof.

7. The method of claim 1, wherein an erection is realized in less then 30 minutes.

8. The method of claim 1, wherein an erection is realized in less than 20 minutes.

9. The method of claim 1, wherein an erection is realized in less than 10 minutes.

10. The method of claim 1, wherein the formulation is a liquid formulation.

11. The method of claim 1, wherein the formulation is a dry powder.

12. The method of claim 1, wherein the formulation comprises a pressurized propellant.

13. The method of claim 1, wherein the formulation comprises 25 mg of sildenafil.

14. The method of claim 1, wherein the formulation comprises 25 to 100 mg of sildenafil.

15. A kit for the treatment of low libido in a woman and erectile dysfunction in a man, comprising:

a hand-held device for the aerosolized delivery of a formulation;

a plurality of containers of an aerosolized formulation comprising sildenafil; and a plurality of container of aerosolizable testosterone.

16. The kit of claim 15, wherein each of the containers of sildenafil comprises 25 mg of aerosolizable sildenafil.

17. The kit of claim 15, wherein each of the containers of sildenafil comprises 25 mg to 10 mg of aerosolizable sildenafil.

* * * * *